(12) United States Patent
Chatel (10) Patent No.: US 12,115,318 B2
(45) Date of Patent: Oct. 15, 2024

(54) STORAGE DEVICE FOR A GUIDE WIRE OR DILATION BALLOON

(71) Applicant: Didier Chatel, Mettray (FR)

(72) Inventor: Didier Chatel, Mettray (FR)

( * ) Notice: Subject to any disclaimer, the term of this patent is extended or adjusted under 35 U.S.C. 154(b) by 323 days.

(21) Appl. No.: 17/535,120

(22) Filed: Nov. 24, 2021

(65) Prior Publication Data

US 2022/0080151 A1 Mar. 17, 2022

Related U.S. Application Data

(63) Continuation-in-part of application No. PCT/FR2020/050856, filed on May 22, 2020.

(30) Foreign Application Priority Data

May 24, 2019 (FR) ...................................... 1905538

(51) Int. Cl.
*A61M 25/00* (2006.01)
*A61M 29/02* (2006.01)
*A61M 25/09* (2006.01)

(52) U.S. Cl.
CPC .......... *A61M 25/002* (2013.01); *A61M 29/02* (2013.01); *A61M 25/09* (2013.01); *A61M 2209/06* (2013.01)

(58) Field of Classification Search
CPC .... A61M 25/002; A61M 25/09; A61M 29/02; A61M 2209/06; A61B 50/22; A61B 50/33
(Continued)

(56) References Cited

U.S. PATENT DOCUMENTS 2,938,624 A * 5/1960 Runkel ............ A61B 17/06123
206/63.3
5,125,416 A * 6/1992 Phillips .................. A61B 50/30
600/585
(Continued)

FOREIGN PATENT DOCUMENTS

WO 02/087996 11/2002

OTHER PUBLICATIONS

International Search Report for PCT/FR2020/050856 dated Sep. 25, 2020, 5 pages.
(Continued)

*Primary Examiner* — Steven A. Reynolds
(74) *Attorney, Agent, or Firm* — NIXON & VANDERHYE (57) ABSTRACT

Storage device for a guide wire or dilation balloon including a tank, and a frame including two walls forming between them an internal volume and including an insertion aperture. The frame includes an opening passing through the frame from one wall to the other, and a slot formed in the internal volume and communicating with the insertion aperture, the slot opening into the opening over part of its perimeter, referred to as open part. The tank includes a positioner configured to place the frame in a stowage position in which the open part of the slot is situated at least partly inside the tank and the insertion aperture extends outside the tank, the tank further including a stop configured to block the translational movement of the frame in directions of insertion and extraction of the guide wire or of the dilation balloon into and out of the frame.

20 Claims, 5 Drawing Sheets

(58) Field of Classification Search
USPC .................................. 206/210, 363, 370, 438
See application file for complete search history.

(56) References Cited

U.S. PATENT DOCUMENTS

| | | | | |
|---|---|---|---|---|
| 5,738,213 | A * | 4/1998 | Whiting | A61M 25/002 206/364 |
| 5,769,222 | A * | 6/1998 | Banerian | A61M 25/09 600/585 |
| 6,547,072 | B2 * | 4/2003 | Whiting | A61M 25/002 206/509 |
| 6,569,106 | B1 * | 5/2003 | Ullman | A61M 25/09 600/585 |
| 6,691,946 | B2 * | 2/2004 | Dannecker | A61M 25/002 242/400.1 |
| 6,902,057 | B2 * | 6/2005 | Duffy | A61M 25/002 206/364 |
| 7,766,162 | B2 * | 8/2010 | Maki | A61M 25/002 600/585 |
| 8,960,432 | B2 * | 2/2015 | Agrawal | A61B 50/20 206/364 |
| 9,427,287 | B2 * | 8/2016 | Lessne | A61B 50/20 |
| 2012/0312703 | A1 * | 12/2012 | Koellhofer | A61B 50/33 206/210 |
| 2016/0206394 | A1 * | 7/2016 | Lampropoulos | B65D 81/22 |
| 2016/0354576 | A1 * | 12/2016 | Klayman | A61M 25/002 |
| 2020/0054855 | A1 * | 2/2020 | Baniasadi | B65D 25/107 |
| 2023/0059137 | A1 * | 2/2023 | Grissom | A61M 25/002 |
| 2023/0181874 | A1 * | 6/2023 | Yamanouchi | A61M 25/02 604/174 |

OTHER PUBLICATIONS

Written Opinion of the ISA for PCT/FR2020/050856 dated Sep. 25, 2020, 6 pages.

* cited by examiner

STORAGE DEVICE FOR A GUIDE WIRE OR DILATION BALLOON

This application is a continuation-in-part of International Application No. PCT/FR2020/050856 filed May 22, 2020 which designated the U.S. and claims priority to FR Patent Application No. 1905538 filed May 24, 2019, the entire contents of each of which are hereby incorporated by reference.

BACKGROUND OF THE INVENTION

Field of the Invention

The present invention in particular concerns devices for intraoperative stowage of guides used in endovascular or endocardial interventional procedures.

Description of the Related Art

In the course of these procedures, it is common to use guides called guide wires. These guides are "lines" that may are may not be made from metal, and are of differing flexibility.

In practice, the guides are packaged in sterile manner and delivered in cases. Removed from the cases, the guides are inserted into the vessels of patients to serve as guides for probes used in performing medical imaging or in therapeutic operations. By way of example, the guides may be used for endovascular procedures or interventions such as: percutaneous aortic valve implantation (TAVI), interventional coronary cardiology, endoprostheses for the treatment of aortic aneurysms, etc.

In general, once they have been removed from the vessels of patients, the guides are coiled and deposited loose in basins containing saline. However, this way of stowing the guides is not optimum in that taking the guides again for a second phase of the interventional procedure requires them to be rummaged for in the "disorder" of the basin.

In this context, guide stowage devices are known which enable the guides to be stored while awaiting later re-use. Document US 2016 020 6394 discloses a device comprising a tank and a frame. The frame comprises several compartments, each compartment being configured to receive a guide. Each guide must be coiled before being stowed in a compartment. Thus, the stowage of the guides requires the use of two hands.

SUMMARY OF THE INVENTION

The present invention is directed to solving at least one of the aforesaid drawbacks.

The invention concerns a guide wire storage device, comprising a tank and at least one removable frame configured to be disposed in the tank, said tank being provided to contain saline. The frame comprises two opposite walls forming between them an internal storage volume and comprises an insertion aperture formed in the internal volume and extending from a first end of the walls towards a second end of the walls which is an opposite end to said first end.

According to the invention, the frame comprises an opening passing through the frame from one wall to the other, and a substantially annular slot formed in the internal volume and communicating with the insertion aperture. The slot opens into the opening over part of its perimeter, designated open part, and is separated from the opening over the rest of its perimeter. The tank comprises positioning means configured to place the frame in a stowage position in which the open part of the slot is situated at least partly inside the tank and the insertion aperture extends outside the tank. The tank further comprises stop means configured to block the translational movement of the frame in directions of insertion and extraction of the guide wire into and out of the frame when the frame is in the stowage position.

The device thus formed enables the guide to be inserted into and extracted from the frame with a single hand since the translational movement of the frame is blocked in the directions of insertion and extraction of the guide wire by virtue of the stop means. The device thus formed is sufficiently stable in stowage position to enable an operator not to have to hold the frame while the guide wire is extracted from and inserted into the frame.

Furthermore, the guide may be inserted easily via the insertion aperture and pushed into the slot.

The annular shape of the slot facilitates the stowage and the coiling of the guide inside the frame. The guide follows the walls of the slot so as to be properly stowed and coiled in the internal volume of the frame.

The stowage of a single guide per frame moreover makes it possible to find each guide easily. Furthermore, at the end of the procedure, the guide may be definitively packaged and stowed in its corresponding frame in order to be thrown away. In other words, each frame and each guide are preferably single-use, which therefore enables clean and orderly packaging for waste disposal.

Furthermore, the device enables the guide to be stowed while soaking in saline. As a matter of fact, as the slot opens into the opening over part of its perimeter, when the guide passes by the open part in the course of being stowed in the frame, said guide is soaked in said saline. This makes it possible to moisten the guides at the time of storage of the guide in the frame as well as when the guide is extracted from the frame.

Lastly, the frame is removable, which makes it possible to move it and manipulate it according to need. The guide thus has no need to be fully removed from the frame to begin to be inserted into the body of a patient. The storage device thus makes it possible to save on guide manipulation and thereby prevent manipulation faults that may be sources of asepsis faults and thus a source of infection; such faults making it necessary to use a new guide. This thus makes it possible to save on the number of guides used per procedure.

According to a feature, the positioning means are adapted to block the translational movement of the frame in a lateral direction.

This makes the frame even more stable in stowage position and thus all the more facilitates the insertion and the extraction of the guide into and from the frame with a single hand.

According to a feature, a clearance separates the positioning means from at least one wall of the frame when the frame is in the stowage position, the clearance being configured such that the walls of the frame abut against the positioning means when the guide wire is extracted from and inserted into the frame.

Translational movement of the frame is thus blocked when the walls abut the positioning means. The clearance thus has the advantage of facilitating the insertion and the positioning of the frame in the tank while making it possible to hold the frame sufficiently stable in the tank, by means of the abutment, for the insertion and the extraction of the guide wire into and from the frame to be carried out with a single hand.

According to a feature, the walls of the frame bear against the positioning means when the frame is in the stowage position.

In other words, the positioning means are configured such that when the frame is in stowage position, there is no clearance between the walls and the positioning means. The frame is thus blocked from lateral translational movement.

According to a feature, the positioning means comprise an assembly member configured to cooperate with the frame through shape complementarity.

The assembly member may be configured to block the lateral translational movement of the frame at least in one direction.

According to a feature, the positioning means are configured to immobilize the frame when the frame is in the stowage position. For example, the positioning means may be one or more clips configured to hold the frame in place.

As the frame is completely immobilized, an operator may then insert or extract the guide wire into or from the frame without being hindered by movement of the frame.

The blocking from translational movement in the lateral direction, going one way, or going both ways or the complete immobilization of the frame enables the frame to be rendered more stable in its stowage position, which facilitates all the more the insertion and the extraction of the frame with one hand.

According to another feature, the open part of the slot comprises bridges spaced along said open part and extending from one side to another side of the slot.

When the guide is inserted into the frame, the guide is soaked in the saline when it is situated at the location of the part of the slot that opens into the opening, that is to say at the location of the portions of the slot that are separated by the bridges.

According to a feature, the slot comprises an upper part formed in an upper portion of the frame and a lower part formed in a lower portion of the frame, the upper and lower parts of the slot being semi-annular, the slot being closed on the upper part and opening into the opening on one or more portions of the lower part, the insertion aperture extending in the upper portion of the frame.

As the aperture extends in the closed upper part of the frame, the guide is properly guided in the slot, thereby avoiding coming out of the frame. As a matter of fact, under its own weight, the guide could have a tendency to come out of the frame if the upper part was open. The lower part may be partially or fully open since the weight of the guide makes it fall towards the bottom of the lower part of the slot.

According to a feature, the opening is substantially circular.

The opening thus follows the substantially annular form of the slot. This enables the guide to be fully moistened by the saline in the part of the slot that opens into the opening.

According to a feature, the walls of the frame are curved.

Thus, a greater part of the frame and thus of the guide may be soaked in the saline located in the tank. Furthermore, this makes it possible to form frames of large size and thus of large diameter without however increasing the height of the frame. Putting the guide in place in a frame of large diameter is thus further facilitated without the height of the frame and thus of the storage device being hindered.

According to a feature, the tank comprises at least two projections extending in a bottom of the tank and configured to receive the frame between them, the projections forming the positioning means, one side of the tank extending facing opposite the second end of the walls of the frame and forming the stop means.

According to a feature, the device comprises an inserter member communicating with the frame through the insertion aperture.

The inserter member avoids a user having to seek the insertion aperture and thereby facilitates the insertion of the guide into the frame.

According to a feature, the inserter member comprises a mounting end complementary to the insertion aperture of the frame, the mounting end being configured to have an insertion fit in the insertion aperture of the frame.

According to a feature, the inserter member has a substantially frusto-conical shape.

As the frusto-conical shape is a flared shape, the guide is thus guided towards the insertion aperture thereby facilitating the insertion of the guide into the frame. The frusto-conical shape gives better visibility to the user towards the insertion aperture.

According to a feature, the inserter member comprises a frusto-conical portion and a beak-like insertion portion extending the frusto-conical portion at a flared end.

As the inserter member has a beak-like portion, this facilitates the guiding of the guide towards the insertion aperture.

According to a feature, the inserter member and the frame are formed as a one-piece member.

According to an arrangement which is original per se, the present invention also provides an assembly comprising a dilation balloon and a storage device for that balloon, the storage device comprising a tank and at least one removable frame configured to be disposed in the tank, said tank being provided to contain saline, said frame comprising two opposite walls forming between them an internal storage volume and comprising an insertion aperture formed in said internal volume and extending from a first end of said walls towards a second end of said walls which is an opposite end to said first end, characterized in that said frame comprises an opening passing through the frame from one wall to the other, and a substantially annular slot formed in said internal volume and communicating with said insertion aperture, said slot opening into the opening over part of its perimeter, designated open part, and being separated from the opening over the rest of its perimeter, and in that said tank comprises positioning means configured to place the frame in a stowage position in which the open part of the slot is situated at least partly inside the tank and the insertion aperture extends outside the tank, said tank further comprising stop means configured to block the translational movement of the frame in directions of insertion and extraction of the dilation balloon into and out of the frame when said frame is in the stowage position.

In other words, the present invention also provides for the use of a storage device as defined above for storing a dilation balloon instead of a guide wire, or a method of storing a dilation balloon which comprises the use of a storage device as defined above.

The optional features defined above for the guide wire storage device may also be implemented with this assembly for storing a dilation balloon.

BRIEF DESCRIPTION OF THE DRAWINGS

Still other particularities and advantages of the invention will appear in the following description with reference to the accompanying drawings which are given by way of non-limiting examples.

DESCRIPTION OF THE PREFERRED EMBODIMENTS

In the following part of the document, the terms longitudinal and lateral are used relatively to the Figures and must in no case be understood restrictively. The longitudinal and lateral directions are perpendicular to each other.

Figure 1:
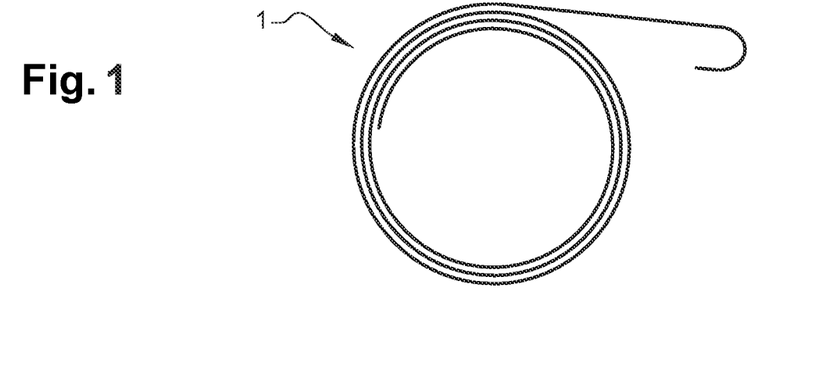
FIG. 1 is a view of a guide wire from above.

FIG. 1 shows a guide wire also referred to as guide 1. FIG. 1 has the form of a line.

The guide 1 is made from a flexible material. The flexibility of the guide 1 enables it to be coiled easily as can be seen in the figure with the object of storing it for example.

The guide 1 is for example of metal or made from any other suitable material.

Figure 2:
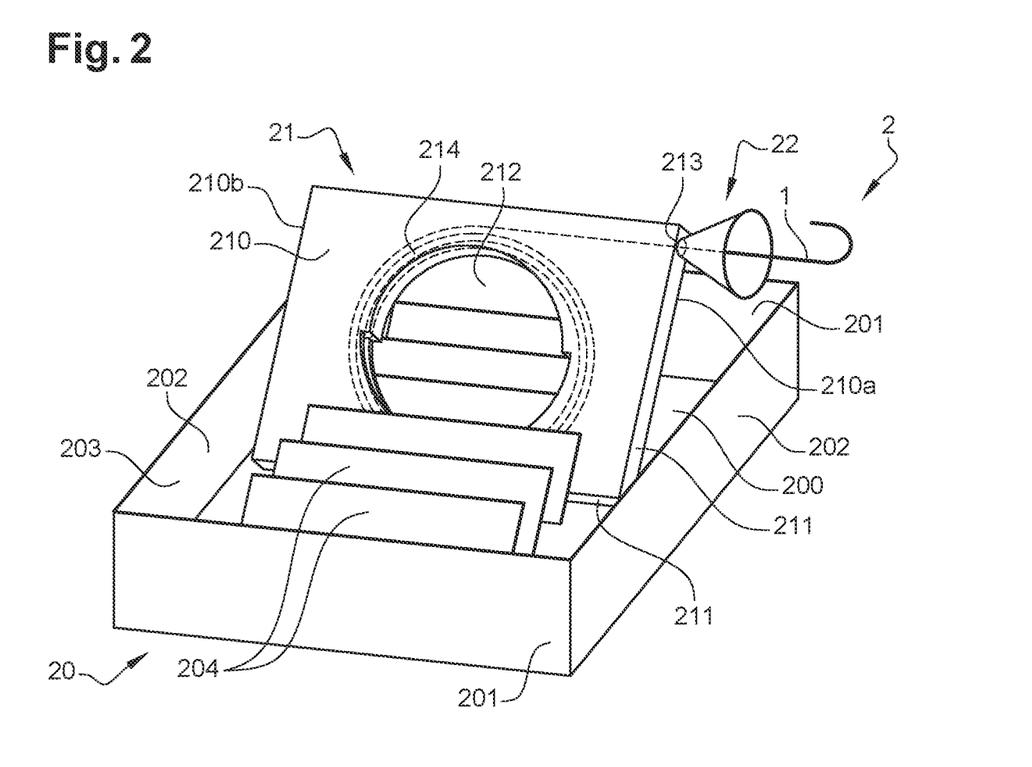
FIG. 2 is a perspective view of a storage device for a guide wire according to a first embodiment.
Figure 3:
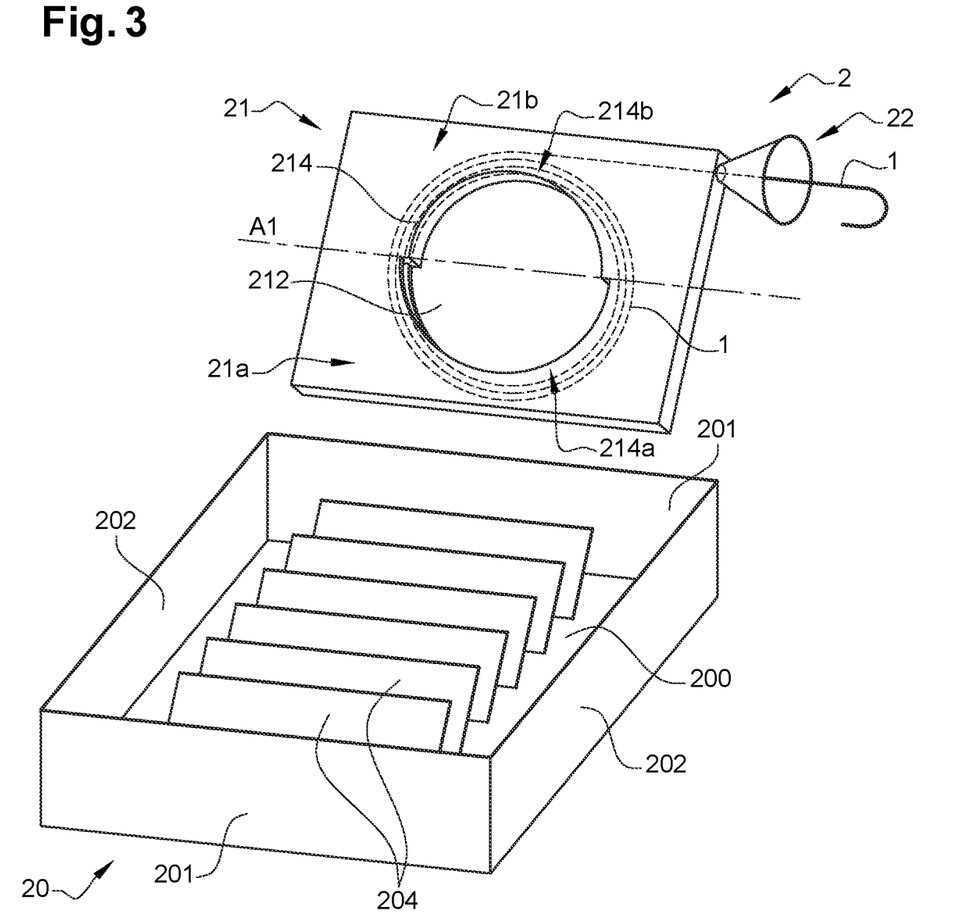
FIG. 3 is an exploded view of FIG. 2.

FIGS. 2 and 3 show a perspective view of a guide storage device 2 according to one embodiment. The storage device 2 comprises a tank 20 and at least one frame 21. In this example, the storage device 2 comprises a single frame 21 and further comprises an inserter member 22.

Of course, the number of frames and inserter members may vary.

The tank 20 here has a form of a parallelepiped box open at the top. The tank 20 comprises a bottom 200, longitudinal sides 201 and lateral sides 202. The bottom 200 has a rectangular shape. The longitudinal sides 201 and lateral sides surround the bottom 200 and extend perpendicularly to the bottom 200.

The longitudinal sides 201 and lateral sides have a sufficient height to enable the tank 20 to be filled with saline (not shown in these Figures).

Of course, the tank 20 may have other shapes. The tank 20 may for example have square or rounded contours.

The tank 20 comprises stop means 203 and positioning means 204. The positioning means 204 are configured to place the frame in a stowage position. The stop means 203 are configured to block the translational movement of the frame 21 in directions of insertion and extraction of the guide wire into and out of the frame 21 when the frame 21 is in the stowage position.

By directions of insertion and extraction of the guide are meant the directions in which the frame moves on insertion and extraction of the guide. In the described example, the directions of insertion and extraction of the guide coincide with the longitudinal direction.

In this example, the tank 20 comprises projections 204. The projections 204 extend in the bottom 200 of the tank 20. The projections 204 here constitute positioning means 204. The projections 204 are six in number here.

The projections 204 here have the form of rectangular plates. The projections 204 extend parallel to each other. A gap or space is formed between each projection. The gap between each projection is at least equal to the thickness of the frame 21. The gap is here the same between all the projections 204. The gap is dimensioned so as to enable the frame 21 to be received between two projections 204 while preventing the frame 21 from translational movement in the lateral direction. In other words, when the frame 21 is disposed in the tank 20, the frame 21 bears against two projections 204. The dimensions of the projections 204 and in particular in this example embodiment, the length of the projections 204, is also chosen so as to prevent the translational movement of the frame 21 in the lateral direction.

Of course, the number, the shape, the disposition and the dimensions of the projections 204 may vary. By way of non-limiting example, there may be clearance between the frame 21 and the projections 204 when the frame 21 is in the stowage position. The positioning means 204 may comprise an assembly member configured to cooperate with the frame 21 by shape complementarity.

In the illustrated embodiment, when the frame 21 is disposed in the tank 20 in the stowage position, the frame 21 is in abutment against the two lateral sides 202. The two lateral sides 202 thus form the stop means 203. The frame 21 is then blocked in both directions of longitudinal translational movement towards the two lateral sides 202.

In this specific example embodiment, the longitudinal direction corresponds to the direction of insertion and extraction of the guide into and from the frame.

Of course, the stop means may be of any other type, shape and number. In another example embodiment, The frame 21 comprises walls 210 which form between them an internal storage volume in which is stowed the guide 1. The frame 21 here comprises two walls 210 and peripheral edges 211. The walls 210 each comprise a first end 210a and a second end 210b which is an opposite end to the first end 210a. The peripheral edges 211 surround the walls 210. The walls 210 are substantially parallel to each other and the peripheral edges 211 are, considered in pairs, substantially parallel to each other such that the frame 21 has a substantially parallelepiped shape.

Figure 4:
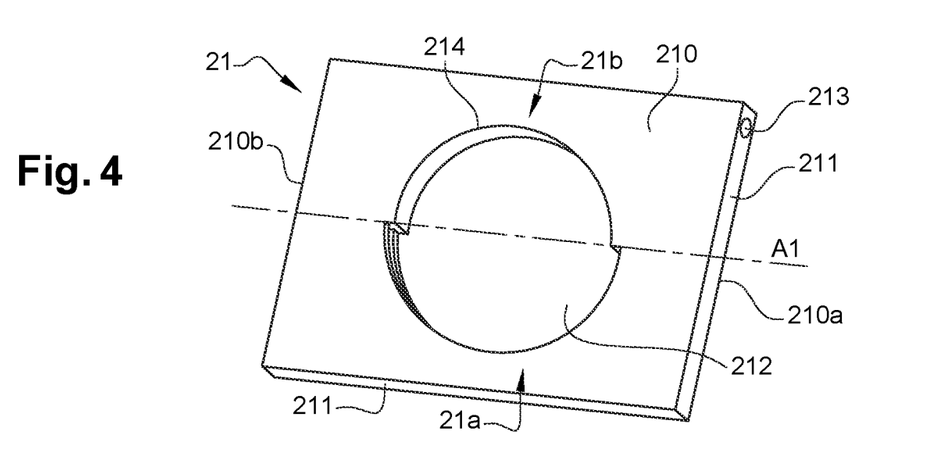
FIG. 4 is a perspective view of a frame of the storage device of FIG. 2.

The frame 21 may be notionally divided into two portions; a lower portion 21a and an upper portion 21b symmetrically separated by a median axis A1 extending parallel to the longitudinal direction.

The frame 21 comprises an opening 212 which can be seen in FIGS. 2, 3 and 4. The opening 212 has a substantially circular contour here. The opening 212 is formed here in the walls 210. The opening 212 is a through hole, that is to say that the opening 212 passes through the walls 210.

The frame 21 also comprises an insertion aperture 213 clearly visible in FIG. 4. The insertion aperture 213 extends from the first end 210a towards the second end 210b of the walls 210. The insertion aperture 213 is formed in one of the peripheral edges 211. The insertion aperture 213 is formed in the upper portion 21b of the frame 2. The insertion aperture 213 is provided to receive the guide 1.

The frame 21 further comprises a slot 214. The slot 214 is formed in the internal volume of the frame 21 and is adjacent to the opening 212. The slot 214 is substantially annular and has substantially the same diameter as a diameter of the opening 212. The slot 214 communicates with the insertion aperture 213. The slot opens into the opening 212 over part of the perimeter of the opening 212, referred to as open part. In other words, the slot 214 is connected to the insertion aperture 213 and is partially open.

The slot 214 comprises a lower part 214a and an upper part 214b separated by the median axis A1. In the embodiment of FIGS. 2, 3 and 4, the slot 214 is fully closed on the upper part 214b. In other words, the upper part 214b of the slot 214 does not communicate with the opening 212. Furthermore, the slot 214 opens into the opening 212 on the lower part 214a.

Of course, the upper part 214b of the slot 214 may be closed only partially, for example by two thirds.

Figure 5:
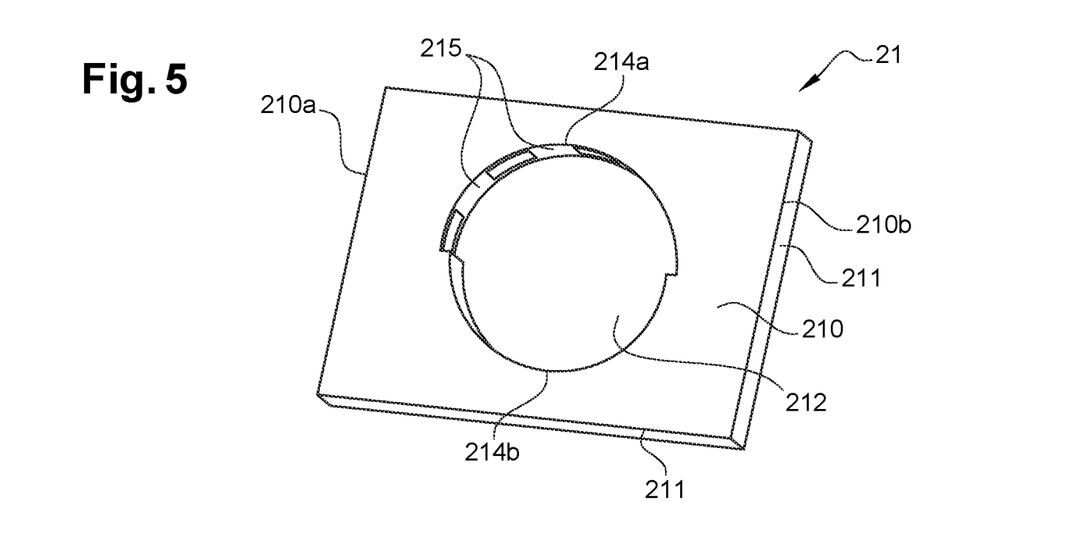
FIG. 5 is an inverted view in perspective of a frame according to a second embodiment.

FIG. 5 represents another embodiment of the frame in which the slot 214 opens into the opening 212 at the location of several portions. In particular, the slot 214 opens at the location of the lower part 214a. A tab or bridge 215 of the frame 21 separates each portion so as to locally close the slot 214. In other words, the part of the slot 214 that opens into the opening, or open part, has bridges 215 spaced along said open part. Each bridge 215 extends from one side to another side of the slot 214.

Figure 6:
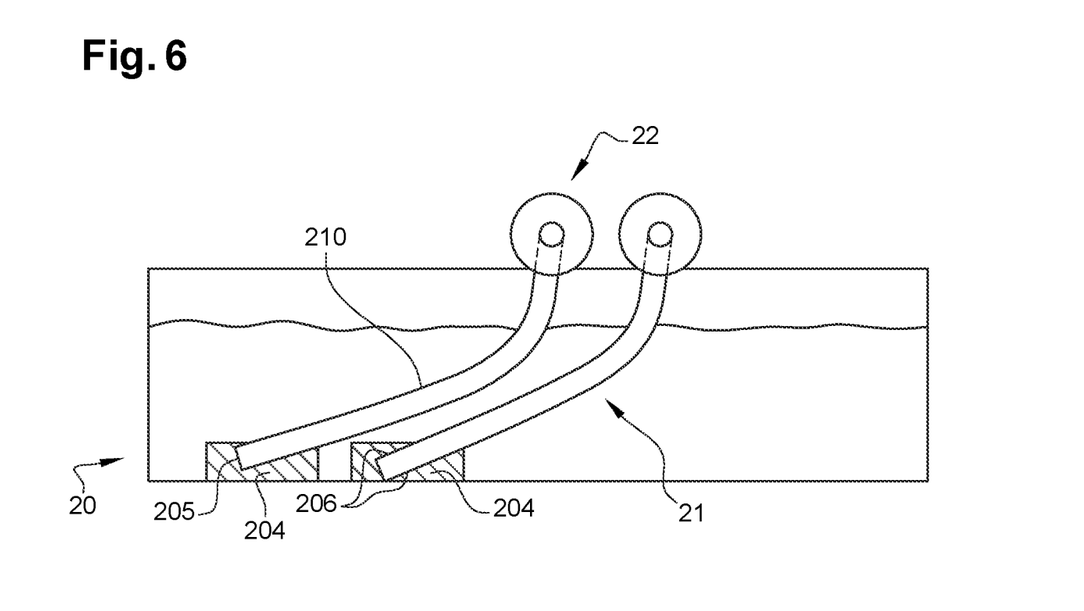
FIG. 6 is a cross-section view of a storage device having a frame according to a third embodiment.

FIG. 6 represents still another embodiment of the frame in which the walls 210 of the frame 21 are curved. When the frame 21 is disposed in the tank 20 in the stowage position, the walls 210 have a convex shape.

In this example, the tank 20 comprises projections 204, each projection 204 comprising a reception zone 205 extending obliquely so as to receive the frame 21. The reception zones 205 are formed so as to enable the arrangement of part of the frame 21 through fitting by shape complementarity. When the frame 21 is in the stowage position, the walls 210 bear against the faces 206 of the reception zone 205.

It is thus possible to form frame with large dimensions and thus in this example having a slot 214 and a large diameter facilitating the putting in place of the guides in the frames, without however increasing the height of the device. This avoids obtaining a storage device having a height causing hindrance in the operational zone if it is too great.

The terms upper and lower are used relatively to FIGS. 2 and 3, and serve merely to facilitate the understanding of the invention.

Figure 7:
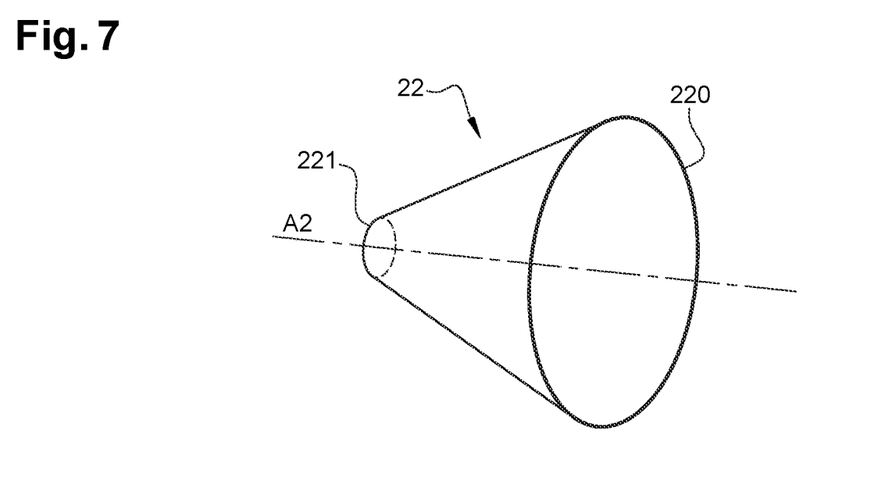
FIG. 7 is a detail view of an inserter member of the storage device of FIG. 2.

FIG. 7 is a detail view representing the inserter member 22 according to the embodiment of FIG. 2. The inserter member 22 is open at both its ends. In the illustrated example, the inserter member 22 has a substantially frusto-conical shape. The inserter member 22 extends around an axis of revolution A2, i.e. the insertion member is symmetrical relative to the axis of revolution A2.

The inserter member 22 comprises a first end 220 and a second end 221 which are open. The first end, also referred to as insertion end 220 or flared end, enables a user to insert the guide 1. The second end, also referred to as mounting end 221, is provided to be mounted to the frame 21 and constitutes the point of entry of the guide 1 into the frame 21.

The mounting end 221 of the inserter member 22 is of circular contour. The mounting end 221 has substantially the same diameter as the diameter of the insertion aperture 213 of the frame 21. The mounting end 221 thus has a shape and dimensions complementary to the shape and dimensions of the insertion aperture 213.

The flared form of the inserter member 22 facilitates the insertion of the guide into the frame 21 and enables the user not to have to aim at the insertion aperture 213 which may be of small size.

Figure 8:
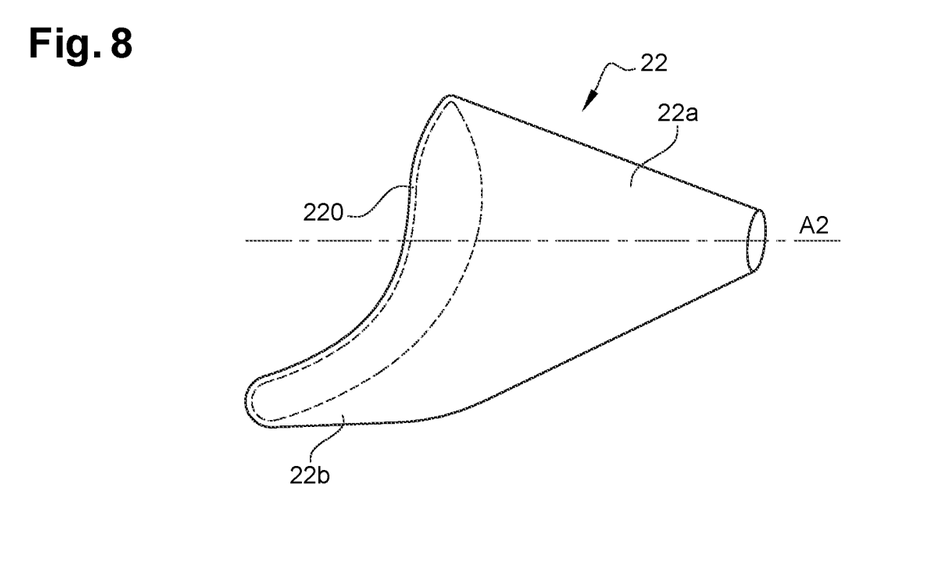
FIG. 8 is a perspective view of an inserter member according to another embodiment.

The inserter member 22 is also shown in FIG. 8 according to another embodiment. The inserter member comprises a frusto-conical portion 22a having a flared end 220 and a mounting end 221, and a beak-like insertion portion 22b extending said frusto-conical portion 22a at the location of the flared end. The frusto-conical portion 22a extends around the axis of revolution A2. In this example, the inserter member 22 is asymmetrical.

The practically flat shape of a portion of the insertion beak-like portion 22b makes it possible to guide the insertion of the guide 1 into the inserter member 22 and towards the insertion aperture 213. The inserter member 22 of the embodiment of FIG. 6 has a sufficiently flared shape to enable easy insertion of the guide 1 into the frame 21.

In these embodiment examples, the inserter member 22 is mounted to the frame 21 with an insertion fit. Of course, the inserter member 22 may be bonded or fixedly attached to the frame 21. The inserter member 22 may also be formed as a once piece member with the frame 21.

In an example embodiment, the storage device 2 and in particular the frame 21 may be produced by 3D printing. In another example, the storage device may be produced by molding. In particular, the frame 21 may be produced by molding. In the latter case, the frame may be divided transversely into two symmetrical parts each formed by molding and bonded together.

On storage of the guide 1 in the storage device 2, the frame 21 is disposed in the tank 20 and positioned by virtue of the positioning means 204. The frame 21 is blocked from translational movement in the insertion and extraction directions of the guide wire by virtue of the stop means 203. Depending on the embodiments, the frame 21 may be fully or partially immobilized in the tank 20.

The inserter member 22 may possibly be mounted to the frame 21. The inserter member 22 may be mounted to the frame 21 before disposing the frame 21 in the tank 20, after disposing the frame 21 in the tank 20 or not be mounted at all.

The guide 1 is next inserted into the frame 21 by a user. The guide 1 may be inserted into the frame 21 either directly through the insertion aperture 213 or by means of the inserter member 22. The guide 1 may be inserted with one hand since the stop means 203 prevent the frame 21 from translational movement in the directions of insertion and extraction of the guide wire 1 into and form the frame 21.

In particular in the embodiment represented in FIGS. 2 and 3, the second end 210b of the walls 210 of the frame 21 is in abutment against the stop means 203. Furthermore, the walls 210 of the frame 21 bear against the positioning means 204. In another example embodiment, the frame 21 may be blocked from longitudinal translational movement in both directions. This facilitates the insertion and withdrawal of the guide with a single hand all the more since the frame 21 is perfectly held fixed in the tank 20.

First of all, the guide 1 follows the slot 214 until a first part of the guide 1 coils through one turn of the slot 214. The user continues to insert the guide 1 such that practically the entirety of the guide 1 becomes coiled in the slot 214 and only a portion remains outside the frame 21 as is clearly visible in FIGS. 2 and 3. In these drawings, the parts of the guide 1 within the internal volume of the frame 21 are shown in dashed line. The portion of the guide 1 remaining outside the frame 21 enables the user to take the guide 1 out of the frame 21 by pulling said portion, for example for its use during an interventional procedure.

As the slot 214 is partially closed, in the examples described, over the whole of the upper part 214b, the guide 1 is well guided along the slot 214 and cannot come out of the opening 212 while it is stored or stowed in the frame.

The tank 20 is filled in advance at least partly with saline. Thus, when the guide 1 is coiled in the frame 21 or withdrawn from the frame 21, practically the entirety of the guide 1 passes by the part or portions that open into the opening 212 so as to enable the guide 1 to be soaked in the saline during the storage procedure.

In the embodiment illustrated in FIG. 6, by virtue of the curved shape of the walls 210, a greater part of the frame 21 is located in the saline of the device and thus a greater part of the guide stored in the frame is immersed in the saline.

The frame 21 is removable and may thus be moved within the tank 20 if required.

If the inserter member 22 is mounted to the frame 21 by insertion fitting, the inserter member 22 is also removable from the frame 21, i.e. the inserter member 22 may be mounted to the frame 21 or removed according to need. This makes it possible to use a same inserter member 22 for several frames 21.

Naturally, the present invention is not limited to the embodiments described and illustrated.

By way of example, the positioning means 204 may also be clips projecting from the bottom 200 of the tank 20.

The stop means 203 may be a projection forming a relief of the bottom 200 of the tank 20 and extending in a lateral direction.

The tank 20 may comprise an intermediate wall or side separating the tank into a first part and a second part. The first part may be configured to receive the frame 21. Thus, the first part of the tank may comprise the positioning means and the stop means. The intermediate side may constitute a stop means. The second part may be configured to form a compartment to receive a disinfectant and/or antiseptic solution which may be used by the operator to moisten the hands or place other tools therein.

The present invention thus provides a storage device enabling the clean, isolated and thereby accounted for stowage of each guide, and making it possible to obtain an operating area which is cleared and orderly. The storage device also makes it possible to avoid faults in asepsis with regard to the guides, and thus inopportune guide changes. The storage of the guide in its frame is carried out easily and with a single hand. Lastly, the final packaging of the single-use guides stowed in the frames at the end of a procedure enables clean packaging for waste disposal of the guides so stowed in the frames.

Figure 9:
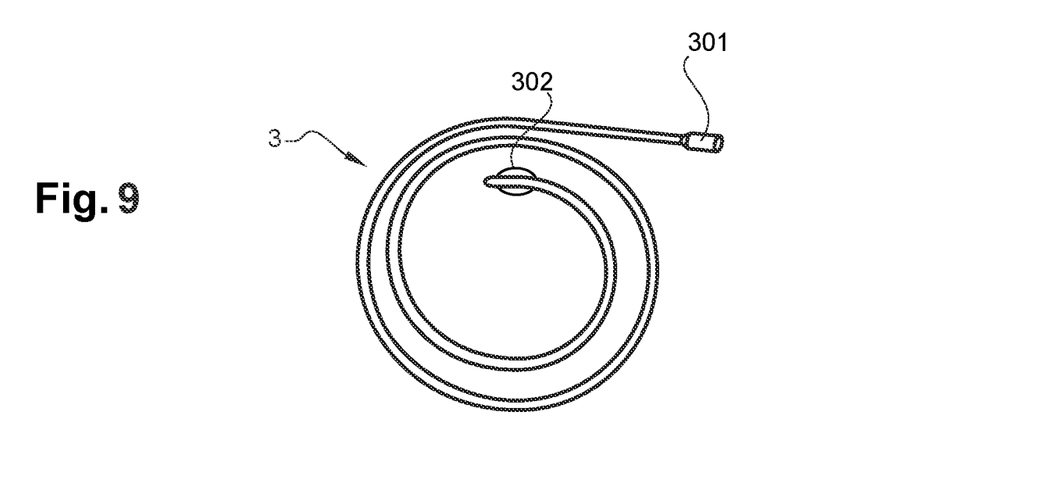
FIG. 9 is a view from above of a dilation balloon.
Figure 10:
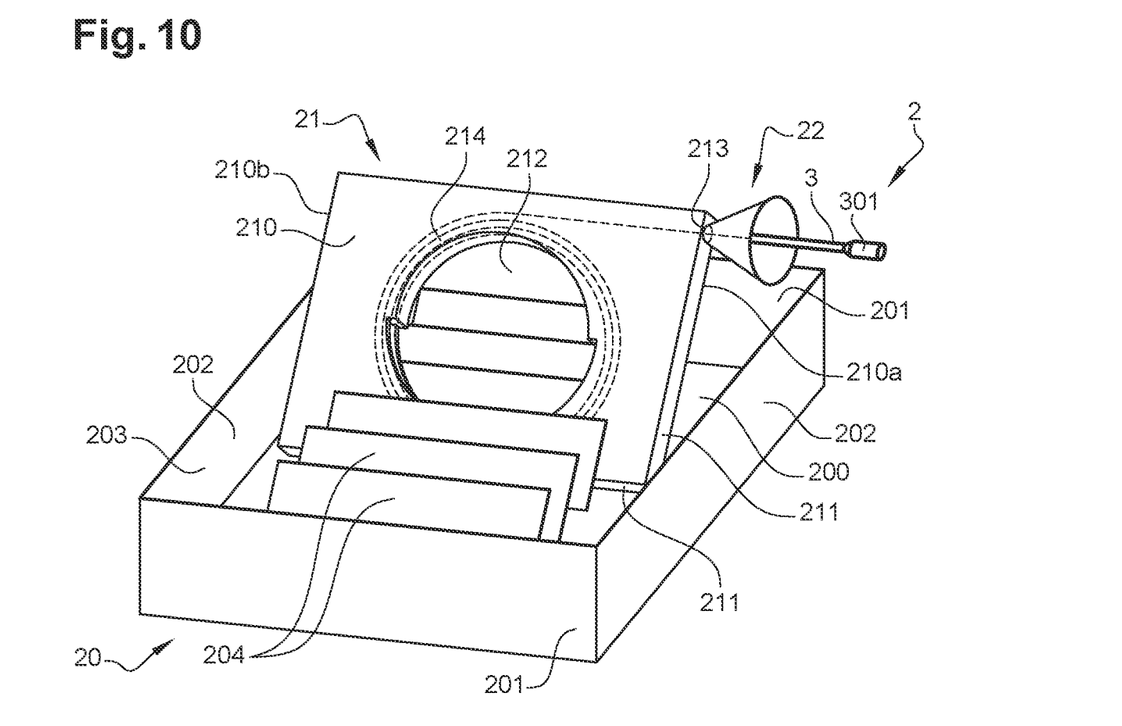
FIG. 10 is a perspective view of a storage device for a dilation balloon according to FIG. 9.

By way of variant, such a storage device may be used for storing a balloon for dilation of an anatomical structure, as is illustrated in FIGS. 9 and 10.

FIG. 9 shows such a dilation balloon 3 provided with an end fitting 301 at one of its free ends and with an inflatable bulb or balloon 302 at its opposite end.

It is usually used to dilate arteries (coronary, femoral, etc.), but may also be used to dilate other anatomical structures.

As can be seen in FIG. 10, it may be stowed in the same way as the guide wire in a storage device 2 of the same kind as that described above for the storage of a guide wire.

It thus also comprises a tank 20 and at least one frame 21, of which the features are the same as those described with reference to the guide wire storage device, with possible dimensional adaptations being the sole difference.

As can also be seen in FIG. 10, the end fitting 301 provided at one of the free ends of the dilation balloon 3 juts beyond the inserter member 22 in storage position.

The invention claimed is:

1. Guide wire storage device, comprising a tank and at least one removable frame configured to be disposed in the tank, said tank being provided to contain saline, said frame comprising two opposite walls forming between them an internal storage volume and comprising an insertion aperture formed in said internal volume and extending from a first end of said walls towards a second end of said walls which is an opposite end to said first end, wherein said frame comprises an opening passing through the frame from one wall to the other, and a substantially annular slot formed in the internal volume and communicating with said insertion aperture, said slot opening into the opening over part of the opening's perimeter, designated open part, and being separated from the opening over the rest of the opening's perimeter, and wherein said tank comprises positioning means configured to place the frame in a stowage position in which the open part of the slot is situated at least partly inside the tank and the insertion aperture extends outside the tank, said tank further comprising stop means configured to block the translational movement of the frame in directions of insertion and extraction of the guide wire into and out of the frame when said frame is in the stowage position.

2. The storage device according to claim 1, wherein the positioning means are adapted to block the translational movement of the frame in a lateral direction.

3. The storage device according to claim 2, wherein the walls of the frame bear against the positioning means when the frame is in the stowage position.

4. The storage device according to claim 2, wherein the positioning means comprise an assembly member configured to cooperate with the frame by shape complementarity.

5. The storage device according to claim 2, wherein the positioning means are configured to immobilize the frame when said frame is in the stowage position.

6. The storage device according to claim 1, wherein the walls of the frame bear against the positioning means when the frame is in the stowage position.

7. The storage device according to claim 6, wherein the positioning means comprise an assembly member configured to cooperate with the frame by shape complementarity.

8. The storage device according to claim 6, wherein the positioning means are configured to immobilize the frame when said frame is in the stowage position.

9. The storage device according to claim 1, wherein the positioning means comprise an assembly member configured to cooperate with the frame by shape complementarity.

10. The storage device according to claim 9, wherein the positioning means are configured to immobilize the frame when said frame is in the stowage position.

11. The storage device according to claim 1, wherein the positioning means are configured to immobilize the frame when said frame is in the stowage position.

12. The storage device according to claim 1, wherein a clearance separates the positioning means from at least one wall of the frame when the frame is in the stowage position, said clearance being configured such that said walls abut against said positioning means when the guide wire is extracted from and inserted into the frame.

13. The storage device according to claim 1, wherein the open part of the slot comprises bridges spaced along said open part and extending from one side to another side of said slot.

14. The storage device according to claim 1, wherein the slot comprises an upper part formed in an upper portion of the frame and a lower part formed in a lower portion of the frame, said upper and lower parts of the slot being semi-annular, said slot being closed on the upper part and opening into the opening on one or more portions of the lower part, said insertion aperture extending in the upper portion of the frame.

15. The storage device according to claim 1, wherein the opening is substantially circular.

16. The storage device according to claim 1, wherein the walls of the frame are curved.

17. The storage device according to claim 1, wherein the device comprises an inserter member communicating with the frame through the insertion aperture.

18. The storage device according to claim 17, wherein said inserter member has a substantially frusto-conical shape.

19. The storage device according to claim 17, wherein said inserter member comprises a frusto-conical portion and a beak-like insertion portion extending said frusto-conical portion at a flared end.

20. Assembly comprising a dilation balloon and a storage device for that ballon, the storage device comprising a tank and at least one removable frame configured to be disposed in the tank, said tank being provided to contain saline, said frame comprising two opposite walls forming between them an internal storage volume and comprising an insertion aperture formed in said internal volume and extending from a first end of said walls towards a second end of said walls which is an opposite end to said first end, wherein said frame comprises an opening passing through the frame from one wall to the other, and a substantially annular slot formed in the internal volume and communicating with said insertion aperture, said slot opening into the opening over part of the opening's perimeter, designated open part, and being separated from the opening over the rest of the opening's perimeter, and wherein said tank comprises positioning means configured to place the frame in a stowage position in which the open part of the slot is situated at least partly inside the tank and the insertion aperture extends outside the tank, said tank further comprising stop means configured to block the translational movement of the frame in directions of insertion and extraction of the dilation balloon into and out of the frame when said frame is in the stowage position.

* * * * *